United States Patent
Blank et al.

(10) Patent No.: US 10,067,077 B2
(45) Date of Patent: Sep. 4, 2018

(54) ROTATIONAL AND AXIAL MOTION SYSTEM AND METHODS OF USE

(71) Applicant: PulseRay Inc., Beaver Dams, NY (US)

(72) Inventors: Basil Eric Blank, Ithaca, NY (US); Jay Schuren, Cambridge, MA (US); Paul Shade, Beavercreek, OH (US); Todd Turner, Yellow Springs, OH (US)

(73) Assignee: PulseRay Inc., Beaver Dams, NY (US)

( * ) Notice: Subject to any disclaimer, the term of this patent is extended or adjusted under 35 U.S.C. 154(b) by 816 days.

(21) Appl. No.: 14/461,582

(22) Filed: Aug. 18, 2014

(65) Prior Publication Data

US 2016/0047722 A1    Feb. 18, 2016

(51) Int. Cl.
*G01N 1/28* (2006.01)
*G01N 23/20025* (2018.01)
*H02N 2/00* (2006.01)
*G01N 23/046* (2018.01)

(52) U.S. Cl.
CPC ..... *G01N 23/20025* (2013.01); *G01N 23/046* (2013.01); *H02N 2/0095* (2013.01); *G01N 2223/3306* (2013.01)

(58) Field of Classification Search
CPC .... F16F 1/18; G01N 3/08; G01N 3/48; G01N 3/16; G01N 2203/0423; G01N 3/064; G01N 2001/1445; G01N 3/22; G01N 2203/0021; G01N 2203/0028; G01N 2203/0037; G01N 2203/0048
See application file for complete search history.

(56) References Cited

U.S. PATENT DOCUMENTS

| | | | | |
|---|---|---|---|---|
| 3,044,289 A | * | 7/1962 | Fleischhauer | G01N 3/307 73/12.01 |
| 3,564,240 A | * | 2/1971 | Thomas, Jr. | G01N 23/20025 269/59 |
| 3,761,146 A | * | 9/1973 | Unno | F16C 32/0644 384/120 |

(Continued)

OTHER PUBLICATIONS

An et al., "NRSF2 Load Frame: Design, Control and Testing", 1 page, downloaded in 2013. Available at http://neutrons.ornl.gov/workshops/sns_hfir_users/posters/An_K_Loadframe-dnh.pdf.

(Continued)

*Primary Examiner* — Harshad R Patel
*Assistant Examiner* — Tran M Tran
(74) *Attorney, Agent, or Firm* — Brown & Michaels, PC

(57) ABSTRACT

A sample manipulator includes a drive system, a pair of flexure plates, and piezoelectric actuators. The drive system preferably includes a pair of drive pulleys on opposite sides of a driven pulley and coupled to the driven pulley by a drive belt. The sample rotates around a rotational axis with the driven pulley. The driven pulley is preferably driven by a pair of drive belts, one being located above the sample, and the other being located below the sample. Fluid bearings provide improved rotation of the driven pulley. The flexure plates are preferably monolithic with a high number of machined flex veins with the side of a tapered threaded screw being used to create the high force required to bend many flexures at the same time for sample motion and to provide fine, precise sub-micron motion control. The piezoelectric actuators provide high-precision control of the load on the sample.

14 Claims, 6 Drawing Sheets

(56) References Cited

U.S. PATENT DOCUMENTS

| | | | | |
|---|---|---|---|---|
| 3,786,676 A * | 1/1974 | Korolyshun | G01N 3/16 | 73/817 |
| 4,349,183 A * | 9/1982 | Wirt | F16F 15/005 | 267/160 |
| 4,393,716 A * | 7/1983 | Clark | G01N 3/16 | 374/51 |
| 4,869,112 A * | 9/1989 | Gram | G01N 3/08 | 73/796 |
| 4,985,973 A * | 1/1991 | Yoshimura | F16F 1/324 | 192/89.25 |
| 5,092,179 A * | 3/1992 | Ferguson | G01N 3/10 | 73/790 |
| 5,095,757 A * | 3/1992 | Larsen | G01N 3/04 | 73/857 |
| 5,138,887 A * | 8/1992 | Pohl | G01N 3/04 | 73/856 |
| 5,176,028 A * | 1/1993 | Humphrey | B29C 65/18 | 374/45 |
| 5,201,489 A * | 4/1993 | Wolf | B29C 33/485 | 248/634 |
| 5,297,441 A * | 3/1994 | Smith | G01N 3/04 | 73/818 |
| 5,425,276 A * | 6/1995 | Gram | G01N 3/32 | 73/781 |
| 5,581,040 A * | 12/1996 | Lin | G01N 3/04 | 73/833 |
| 5,945,607 A * | 8/1999 | Peppel | G01N 3/04 | 73/831 |
| 5,948,994 A * | 9/1999 | Jen | G01N 3/08 | 73/796 |
| 5,952,581 A * | 9/1999 | Lammers | G01M 17/04 | 73/650 |
| 5,959,215 A * | 9/1999 | Ono | G01N 3/36 | 73/789 |
| 5,993,058 A * | 11/1999 | Rochard | H05B 6/105 | 219/632 |
| 6,058,784 A * | 5/2000 | Carroll | G01N 3/10 | 73/831 |
| 6,301,972 B1 * | 10/2001 | Hall | G01N 3/04 | 73/857 |
| 6,398,444 B1 * | 6/2002 | Salmela | F16F 15/073 | 267/160 |
| 6,422,090 B1 * | 7/2002 | Ferguson | B21J 9/20 | 73/795 |
| 6,443,183 B1 * | 9/2002 | Roorda | F16F 1/027 | 137/529 |
| 6,526,837 B1 * | 3/2003 | Grote | G01N 3/04 | 73/856 |
| 6,629,466 B2 * | 10/2003 | Grote | G01N 3/04 | 73/857 |
| 6,679,124 B2 * | 1/2004 | Oliver | G01N 3/08 | 73/796 |
| 6,732,591 B2 * | 5/2004 | Miles | G01N 3/32 | 73/808 |
| 6,789,486 B2 | 9/2004 | Poulsen | | |
| 6,813,960 B1 * | 11/2004 | Owen | G01N 3/32 | 73/794 |
| 6,888,920 B2 * | 5/2005 | Blank | G01N 23/20016 | 359/811 |
| 7,204,152 B2 * | 4/2007 | Woodward | G01N 3/32 | 73/794 |
| 7,204,153 B2 * | 4/2007 | Phipps | G01N 3/04 | 73/794 |
| 7,363,822 B2 * | 4/2008 | Lindeman | G01N 3/18 | 73/818 |
| 7,458,278 B1 * | 12/2008 | Lin | G01L 5/24 | 73/843 |
| 7,513,168 B2 * | 4/2009 | Alba | G01N 3/16 | 73/818 |
| 7,543,506 B2 * | 6/2009 | Merendino, Sr. | G01N 3/38 | 73/777 |
| 7,568,397 B2 * | 8/2009 | Merendino, Sr. | G01N 3/04 | 73/818 |
| 7,739,919 B2 * | 6/2010 | Lemmer | G01N 3/04 | 73/857 |
| 8,443,679 B2 * | 5/2013 | Trautwein | G01N 3/165 | 73/825 |
| 8,561,474 B2 * | 10/2013 | Secq | E21B 21/08 | 73/825 |
| 8,591,117 B2 * | 11/2013 | Giraud | F16C 27/045 | 384/535 |
| 9,032,813 B2 * | 5/2015 | Matsumoto | G01N 3/22 | 73/848 |
| 9,273,413 B2 * | 3/2016 | Krishnan | C30B 25/12 | |
| 9,402,588 B2 * | 8/2016 | Mueller | A61B 6/4488 | |
| 9,535,078 B2 * | 1/2017 | Dorman | G01N 35/00 | |
| 9,599,578 B2 * | 3/2017 | Yanagita | F16C 17/107 | |
| 2002/0017146 A1 * | 2/2002 | Oliver | G01N 3/08 | 73/856 |
| 2004/0020287 A1 * | 2/2004 | Sentmanat | G01N 3/08 | 73/261 |
| 2005/0011275 A1 * | 1/2005 | Ferguson | G01N 3/04 | 73/818 |
| 2006/0180577 A1 * | 8/2006 | Lindeman | G01N 3/18 | 219/50 |
| 2007/0227259 A1 * | 10/2007 | Alba | G01N 3/16 | 73/831 |
| 2009/0314107 A1 * | 12/2009 | Yakimoski | G01N 3/08 | 73/865.6 |
| 2015/0243470 A1 * | 8/2015 | Fish | H01J 37/20 | 250/428 |
| 2016/0061703 A1 * | 3/2016 | Yoon | G01N 3/56 | 73/10 |
| 2017/0176319 A1 * | 6/2017 | Dube | G01N 19/02 | |

OTHER PUBLICATIONS

Awtar, "Synthesis and Analysis of Parallel Kinematic XY Flexure Mechanisms", Massachusetts Institute of Technology Ph.D. Thesis, 2004, 198 pages.

Awtar, "Fabrication, Assembly and Testing of a new X-Y Flexure Stage with substantially zero Parasitic Error Motions", 14 pages, downloaded in 2013. Available at http://www-personal.umich.edu/~awtar/PHD/report.pdf.

Bari, "X-Ray Computed Tomography of Mechanical Deformation in Sand Under Compression", Oklahoma State University Masters' Thesis, 2010, 67 pages.

Breunig et al., "A Servo-Mechanical Load Frame for in situ, Non-invasive, Imaging of Damage Development", 18th Annual Conference on Composites and Advanced Ceramics, Cocoa Beach, FL, 1994, 10 pages.

Buffiere et al., "In Situ Experiments with X-ray Tomography: an Attractive Tool for Experimental Mechanics", Experimental Mechanics, vol. 50, pp. 289-305, 2010.

Chang, "Development of a Monolithic Sub-Micron Precision Linear-Motion Mechanism", San Diego State University Masters' Thesis, 2010, 71 pages.

Chang et al. "An Ultra-Precision XYθZ Piezo-Micropositioner Part I: Design and Analysis", IEEE Transactions on Ultrasonics, Ferroelectrics, and Frequency Control, vol. 46, pp. 897-905, 1999.

Choi et al., "A compliant parallel mechanism with flexure-based joint chains for two translations", International Journal of Precision Engineering and Manufacturing, vol. 13, pp. 1625-1632, 2012.

Dunsmuir, "X-Ray Microtomography", 8 pages, downloaded in 2013. Available at http://www.bnl.gov/ps/nsls/newsroom/publications/otherpubs/imaging/workshopdunsmuir.pdf.

Holden et al., ed., "'Current State and Future of Neutron Stress Diffractometers' Workshop and its conclusions regarding the Residual Stress Program development at the Australian OPAL Research Reactor", 2012, 31 pages.

Li et al., "Modeling and performance evaluation of a flexure-based XY parallel micromanipulator", Mechanism and Machine Theory, vol. 44, pp. 2127-2152, 2009.

(56) References Cited

OTHER PUBLICATIONS

Ludwig et al., "Characterization of Polycrystalline Materials Using Synchrotron X-ray Imaging and Diffraction Techniques", JOM, vol. 62, pp. 22-28, 2010.

McCarthy, "Limitations of Flexures", 6 pages, downloaded in 2013. Available at http://www.dovermotion.com/Downloads/KnowledgeCenter/flexures.pdf.

Reiche et al., "A furnace with rotating load frame for in situ high temperature deformation and creep experiments in a neutron diffraction beam line", Review of Scientific Instruments, vol. 83, 053901, 2012, 7 pages.

Uesugi et al., "Development of high spatial resolution X-ray CT system at PL47XU in Spring-8", Nuclear Instruments and Methods in Physics Research Section A: Accelerators, Spectrometers, Detectors and Associated Equipment, vol. 467-468, pp. 853-856, 2001.

Wang et al., "High-pressure x-ray tomography microscope: Synchrotron computed microtomography at high pressure and temperature", Review of Scientific Instruments, vol. 76, 073709, 2005, 7 pages.

Wenjie et al., "A flexure-based 4-DOF coaxial alignment system: Design and application", 11th International Conference on Control Automation Robotics & Vision, pp. 1755-1759, 2010.

Wildenschild et al., "X-ray imaging and analysis techniques for quantifying pore-scale structure and processes in subsurface porous medium systems", Advances in Water Resources, vol. 51, pp. 217-246, 2013.

Wright et al., "High Resolution Computed Tomography for Modelling Laminate Damage", 2009, 10 pages. Available at http://www.iccm-central.org/Proceedings/ICCM17proceedings/Themes/TSAI/T1.4%20Wright.pdf.

Wyss et al., "Sample handler for x-ray tomographic microscopy and image-guided failure assessment", Review of Scientific Instruments, vol. 76, 076106, 2005, 3 pages.

Yan et al., "From Single Grains to Texture", Advanced Engineering Materials, vol. 11, pp. 771-773, 2009.

Zhao et al., "High-pressure neutron diffraction studies at LANSCE", Applied Physics A, vol. 99, pp. 585-599, 2010.

"Flexures", 16 pages, downloaded in 2013. Available at http://www.mech.utah.edu/~me7960/lectures/Topic12-Flexures.pdf.

"Industrial Process Gamma Tomography: Final report of a coordinated research project 2003-2007", International Atomic Energy Agency, 2008, 153 pages.

"P-734 Single-Module, XY Piezo Flexure NanoPositioners and Scanners", 2 pages, downloaded in 2013. Available at http://katalog.physikinstrumente.com/Links/topicPDFs/2-28.pdf.

"Practical Exact-Constraint Design", pp. 174-224, downloaded in 2013. Available at http://pergatory.mit.edu/kinematiccouplings/documents/Theses/hale_thesis/Practical_Exact_Constraint.pdf.

ThorLabs CP1XY—Cage XY Flexure Adjustment Plate, 1 page, saved in 2013. Available at http://www.thorlabs.com/thorproduct.cfm?partnumber=CP1XY.

* cited by examiner

ROTATIONAL AND AXIAL MOTION SYSTEM AND METHODS OF USE

ACKNOWLEDGMENT OF GOVERNMENT SUPPORT

This invention was made with Government support under Prime Contract No. FA8650-10-D-5226, awarded by USAF/AFMC, Det 1 AFRL Wright-Patterson AFB. The government has certain rights in the invention.

BACKGROUND OF THE INVENTION

Field of the Invention

The invention pertains to the field of high-precision measuring devices. More particularly, the invention pertains to a high-precision system for loading and for rotational and axial movement of a sample.

Description of Related Art

There are many fields where precise sample control, positioning, and manipulation is critical, including, but not limited to, tomography, microscopy, materials testing, and micro-machining.

Tomography is a non-destructive, non-invasive method of imaging a three-dimensional object. A tomograph images a sample by sectioning through the sample using a penetrating wave. X-rays or gamma rays are commonly used as the penetrating wave, but radio-frequency waves, electron-positron annihilation, electrons, ions, magnetic particles, or neutrons may also be used. A mathematical process called tomographic reconstruction is used to generate an image from the data produced by sectioning the sample by the penetrating wave. X-ray computed tomography, computed tomography (CT scan), or computed axial tomography (CAT scan) are commonly used medical imaging procedures.

In the case of x-ray tomography, the imaging of a sample depends on the absorption of x-rays by the sample. The sample is placed between the x-ray source and an x-ray detector, which measures the attenuation in the transmitted rays. Either the detector or the sample may be fixed in location. With conventional fixed detector systems, the stage on which the sample is mounted is rotated up to 180 or 360 degrees. Radiographs of the sample are collected on the detector at different time points as the stage rotates. The image obtained at each angle includes a matrix of pixels. The intensity of each pixel is a function of the linear absorption coefficient, which in turn depends on the chemical and physical makeup of the sample. Back-propagation and other advanced de-convolution methods may be used to provide a three-dimensional intensity file to reconstruct an image representing the sample from the radiographs, which is conventionally done one slice at a time. A complete three-dimensional image is conventionally obtained by stacking axial slices together.

The resolution of a tomograph is dependent on the fineness of the control of the positioning and movement of the sample stage and the beam source. The best conventional high-precision tomographs only have a measurement resolution to the micron level.

In materials testing, it is advantageous to perform tests on a sample that is under a controlled load, such as a tensile load or a compressive load. It is important to be able to apply a controlled, known load to a sample being tested.

SUMMARY OF THE INVENTION

A sample manipulator includes a drive system, a pair of flexure plates, and piezoelectric actuators. The drive system preferably includes a pair of drive pulleys on opposite sides of a driven pulley and coupled to the driven pulley by a drive belt. The sample rotates around a rotational axis with the driven pulley. The driven pulley is preferably driven by a pair of drive belts, one being located above the sample, and the other being located below the sample. Fluid bearings provide improved rotation of the driven pulley. The flexure plates are preferably monolithic with a high number of machined flex veins with the side of a tapered threaded screw being used to create the high force required to bend many flexures at the same time for sample motion and to provide fine, precise sub-micron motion control for centering the sample on the rotational axis. The piezoelectric actuators provide high-precision control of the load on the sample and allow high precision sample translation along the rotational axis. The piezoelectric actuators also allow high rate cyclic fatigue testing of the sample.

DETAILED DESCRIPTION OF THE INVENTION

Figure 1:
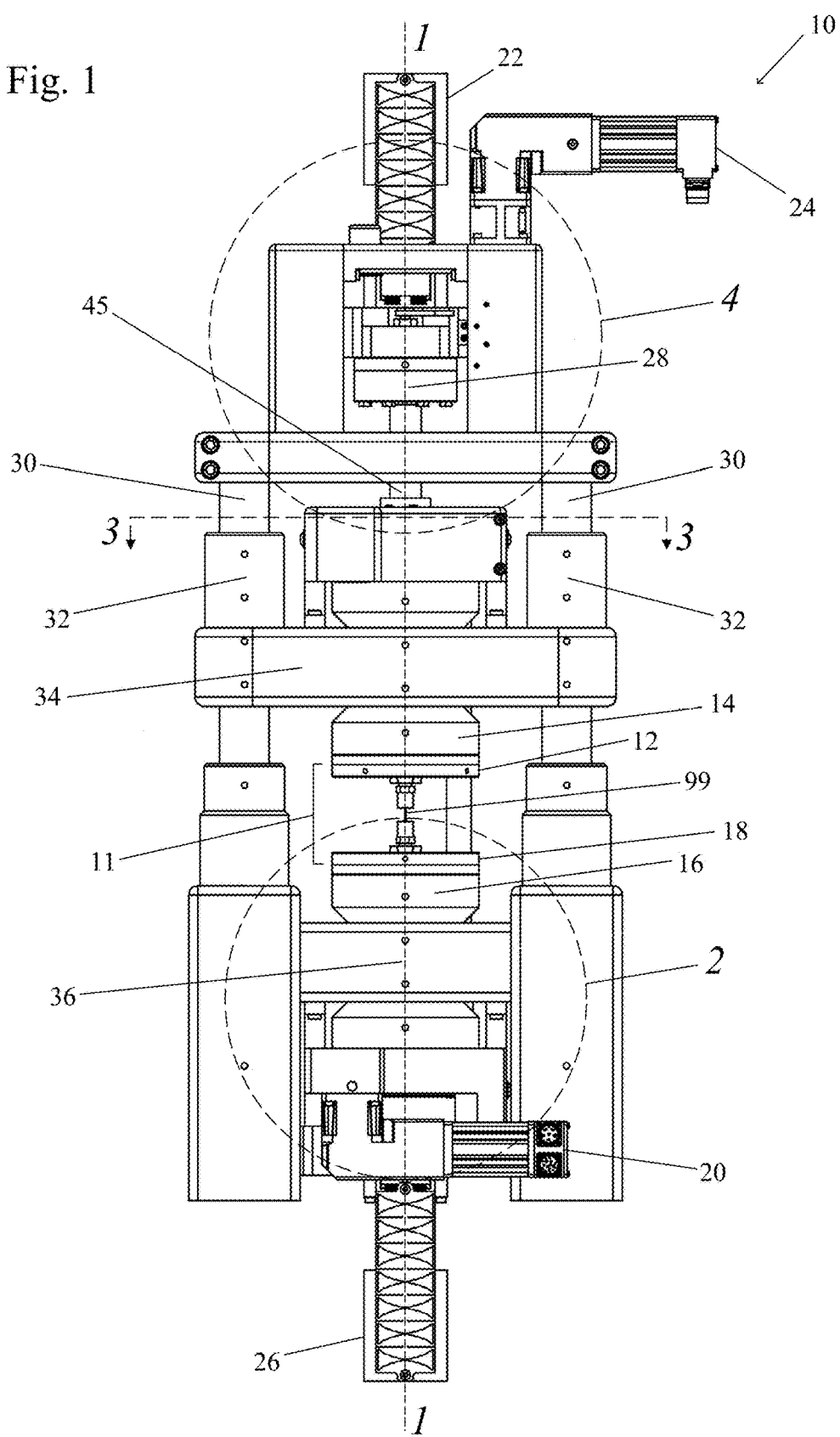
FIG. 1 shows a front view of a sample manipulator in an embodiment of the present invention.

A rotational and axial motion system is capable of high-precision manipulation of a sample, including placing the sample under tension, compression, and a no-load condition with a high degree of precision. In some embodiments, the load is a static load. In other embodiments, the load is dynamic in that the system dynamically controls the tension, compression, and rotation of the sample. This allows variable, programmable, cyclic or non-cyclic, fully controlled dynamic testing of a sample. The sample manipulator of the rotational and axial motion system allows 360 degrees of continuous sample rotation or any incremental steps in between. The sample manipulator is preferably an extreme-precision coaxial, two spool rotation axis, fluid flow bearing, rotation and linear axial motion sample manipulator.

The sample manipulator preferably includes a drive system, a pair of flexure plates, and piezoelectric actuators. The drive system preferably includes a pair of drive pulleys on opposite sides of a driven pulley and coupled to the driven pulley by a drive belt. The sample rotates around a rotational axis with the driven pulley. The driven pulley is preferably driven by a pair of drive belts, one being located above the sample, and the other being located below the sample. Fluid bearings provide improved rotation of the driven pulley. The flexure plates are preferably monolithic with a high number of machined flex veins with the side of a tapered threaded screw being used to create the high force required to bend many flexures at the same time for sample motion and to provide fine, precise sub-micron motion control. The piezoelectric actuators provide high-precision control of the load on the sample.

The sample manipulator is preferably capable of precision angular motion from small angular steps to continuous rotation.

Sample tension and compression measurements may be made during sample rotation or on a stationary sample.

The sample manipulator spools are preferably fluid flow bearing assemblies which can resist axial motion and radial motion.

The use of fluid flow bearings allows orders of magnitude better resolution than conventional instruments with conventional bearings, because as the precession of a system improves, the angular measurements also improve.

The drive system also aids in creating a lower precession or greater concentricity. By using a pulley on both sides of the driven pulley, which is attached to the fluid flow bearing shaft, equal and opposite forces are created, which cancel each other when the system is driving.

Although the sample manipulator is primarily described as being part of a high-precision tomography system, the sample manipulator may be used in any application where high-precision control and manipulation of a sample is desired within the spirit of the present invention, including, but not limited to, tomography, microscopy, materials testing, and micro-machining. A high-precision tomography system preferably includes a penetrating wave source, a detector, the sample manipulator, and a processor. The penetrating wave source in the high-precision tomography system may be any conventional or custom source that produces a penetrating wave for tomographic imaging. The penetrating wave may be of any type used or useable in tomography, including, but not limited to, x-ray, gamma ray, radio-frequency, electron-positron annihilation, electron, ion, magnetic particle, or neutron. The detector may be any conventional or custom detector that detects the penetrating wave. The processor may be any conventional or custom processor, including, but not limited to, a desktop computer or a laptop computer, that receives the tomographic wave data from the detector and directs the penetrating wave source, the detector, and the tomographic sample manipulator. The processor preferably includes software and hardware that directs the penetrating wave source, the detector, and the sample manipulator and converts the tomographic wave data into a tomogram either automatically or under the direction of a user.

For a system with very high precision manipulation, it is also necessary to precisely center a sample in the instrument. The flexure plates preferably allow sub-micron centering of a sample with the ability to handle large forces perpendicular to the face of the flexure alignment plate. This is necessary to enable the tension and compression testing with the instrument.

The high-precision system also preferably has the ability to subject the sample to cyclic fatigue testing rapidly using piezoelectric actuators. Conventional tomographs use hydraulic actuator systems for sample loading. The piezoelectric actuators create orders of magnitude more precise sample loading by having many orders of magnitude better resolution relative to hydraulic systems.

This high-precision system also has the ability to move the sample along the rotational axis using the duel piezoelectric actuators. The duel piezoelectric actuators, in conjunction with linear fluid flow bushings, create nanometer-scale resolution sample translation for exploring a new region of the sample. Conventional systems have no better than one-micron resolution.

An advantage of duel piezoelectric actuators in conjunction with linear fluid bushings, preferably linear air bushings, which hold the moving load supports of the load frame, is that the sample may be translated along the rotational axis with an off axis precision on the order of tens of nanometers. Conventional precision is no better than one micron.

The flexure sample alignment stage preferably includes at least one, and more preferably includes all, of the following features:

1. A high-load, sub-micron adjustment, single-axis or multi-axis sample alignment stage, in contrast to conventional small sample low load stages;
2. A monolithic structure with machined veins, which allow manual or motorized adjustment, which flexes the veins for sample motion, such as to center a sample on a rotational stage;
3. High stiffness along one or more axes and adjustability along one or more axes, in contrast to conventional low torsional stiffness, low off-axis stiffness, low load-direction stiffness stages;
4. A high number of flex veins to carry the load, in contrast to conventional single-axis or multi-axis monolithic flexure plates using a small number of flex veins to carry the load; and
5. Use of the side of a tapered threaded screw to create the high force required to bend many flexures at the same time for sample motion and to provide fine, precise sub-micron motion control, in contrast to conventional use of the tip of a threaded screw to bend the flexures for sample movement.

In a preferred embodiment, a sample manipulator includes at least one, and preferably all of the following features:

1. Reduced sample radial precession using fluid flow bushings instead of roller bearings;
2. Reduced sample axial precession using fluid flow bearings instead of using thrust roller bearings;
3. Increased sample angular precision as a result of the reduced sample radial precession and reduced sample axial precession;
4. Sample alignments using two-axis flexure plates;
5. Reduced sample precessions using double drive pulleys, which reduce off axis load on the sample fluid flow bushing rotational shaft;
6. Sample cyclic fatigue testing using piezoelectric actuators;
7. Sample loading using piezoelectric actuator; and
8. Sample translation using piezoelectric actuators and fluid flow bushings.

FIG. 1 shows a sample manipulator 10. A sample stage 11 holds a sample 99, which may be maintained under tension, under compression, or under no load by the manipulator 10. The sample stage 11 includes a sample holder holding two ends of the sample 99. A sample centering flexure plate 12, mounted to the end of a top fluid bearing spool 14 on a side facing the sample 99, keeps the sample 99 centered on the axis of rotation of the manipulator 10, also referred to herein as the rotational axis 1. A bottom fluid bearing spool 16 sits below the sample and includes a sample rotation fluid flow bearing and bushing combination more visible in FIG. 2. A sample alignment flexure plate 18 is mounted to the end of the bottom bearing spool 16 facing the sample 99. Preferably, the sample centering flexure plate 12 and the sample alignment flexure plate 18 are substantially identical in shape and design. The bottom bearing is driven by the sample rotation motor 20 and the top bearing is a follower, although in an alternative embodiment the top bearing may be driven with the bottom bearing being the follower. Axial motion is controlled by a top axial motion cross support piezoelectric actuator 22 through a fluid flow rotation shaft 45, a top axial motion cross support drive motor 24, and a bottom axial motion cross support piezoelectric actuator 26. A sample load cell 28, which accurately measures the tension and compression loads on the sample, sits below the top axial motion cross support piezoelectric actuator 22. A pair of load frame stationary fluid flow bushing shafts 30 sit above a pair of top vertical motion cross support fluid flow bushings 32, which are coupled to each other by a top vertical motion cross support 34. A bottom vertical motion cross support 36 sits below the bottom fluid bearing spool 16.

Figure 2:
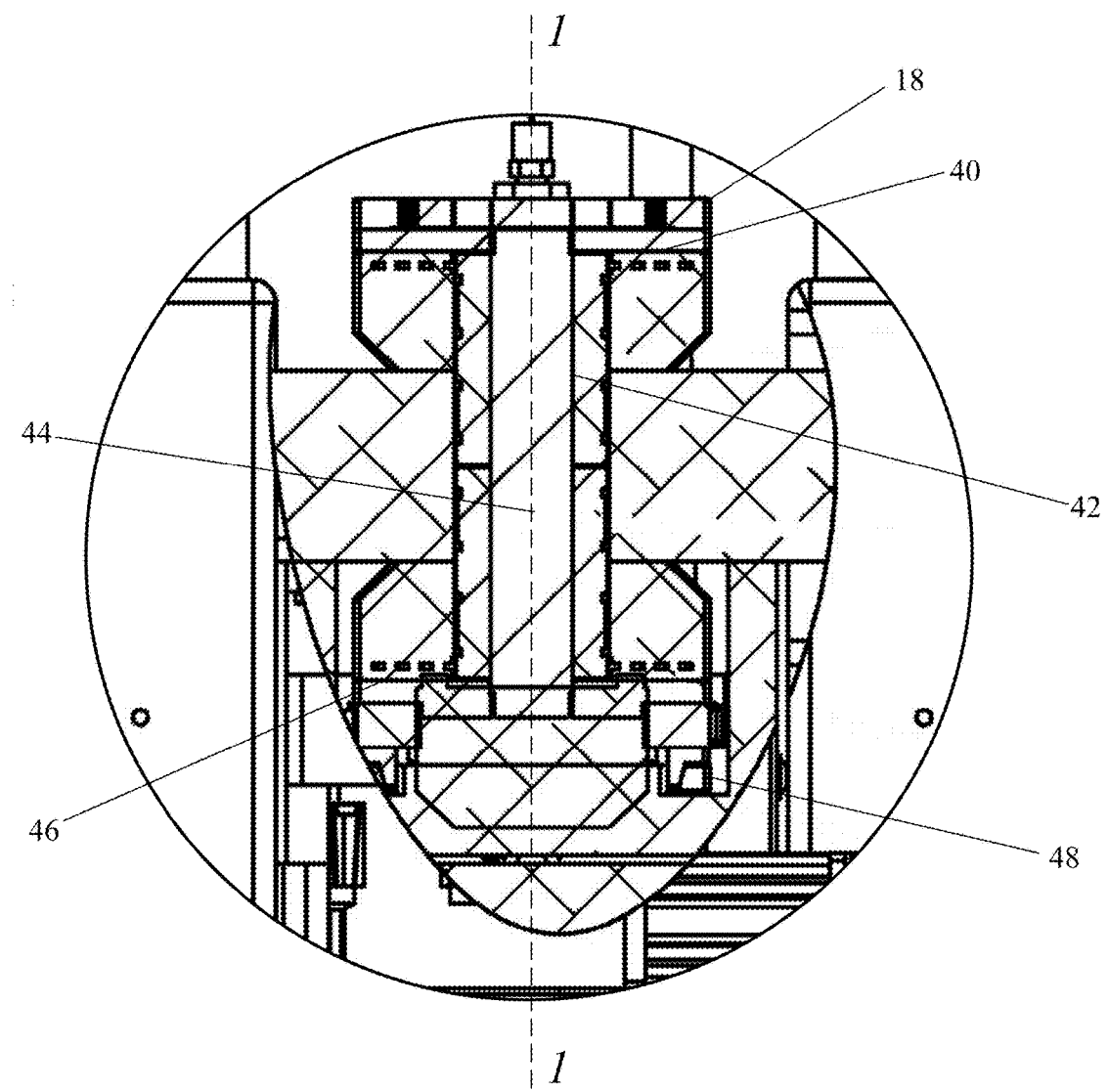
FIG. 2 shows a broken out sectional view within circle 2 of FIG. 1 showing the spool assembly.

In the close-up portion visible in FIG. 2, a cutaway view of the sample alignment flexure plate 18 is shown. Below the sample alignment flexure plate 18 sits the spool assembly, which includes a fluid flow bearing surface for axial load 40, a fluid flow bushing surface for radial load 42, a fluid flow rotation shaft 44, a fluid flow surface for axial load 46, and a rotary angular measurement encoder 48. The fluid in the spool assembly may be a liquid or a gas. In some embodiments, the fluid is compressed air. In a preferred embodiment, the normal operating pressure is about 60 psi. In other embodiments, the fluid is an oil, preferably a lubricating oil. The use of compressed air may be more favorable for lower loads, whereas the use of oil may be more favorable for higher loads.

Figure 3:
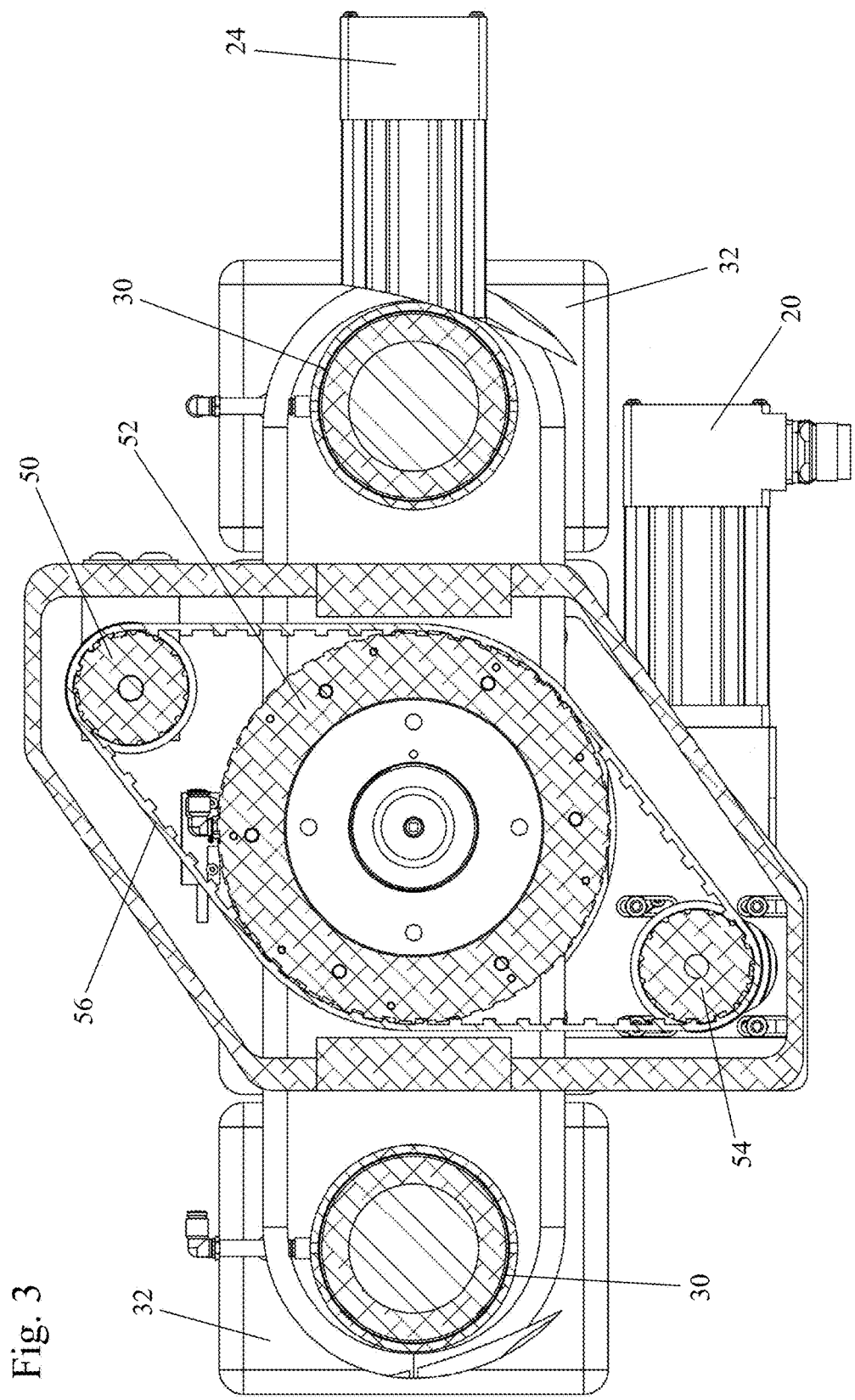
FIG. 3 shows a partial cross sectional top view along line 3-3 of FIG. 1 showing the dual drive assembly.

Referring to the partial cross sectional view of FIG. 3, the drive system includes a drive pulley 50, a rotational axis driven pulley 52, an idle pulley 54, and a drive belt 56. The sample rotation motor 20 (see FIG. 1) drives the drive pulley 50 and the idle pulley 54, and the drive belt 56 transfers rotation of the drive pulley 50 and the idle pulley 54 to the rotational axis driven pulley 52. Equal and opposite belt loads on the rotational axis driven pulley 52 by use of a drive pulley 50 and an idle pulley 54 on both sides of the rotational axis driven pulley 52 reduces rotational axis runout.

Figure 4:
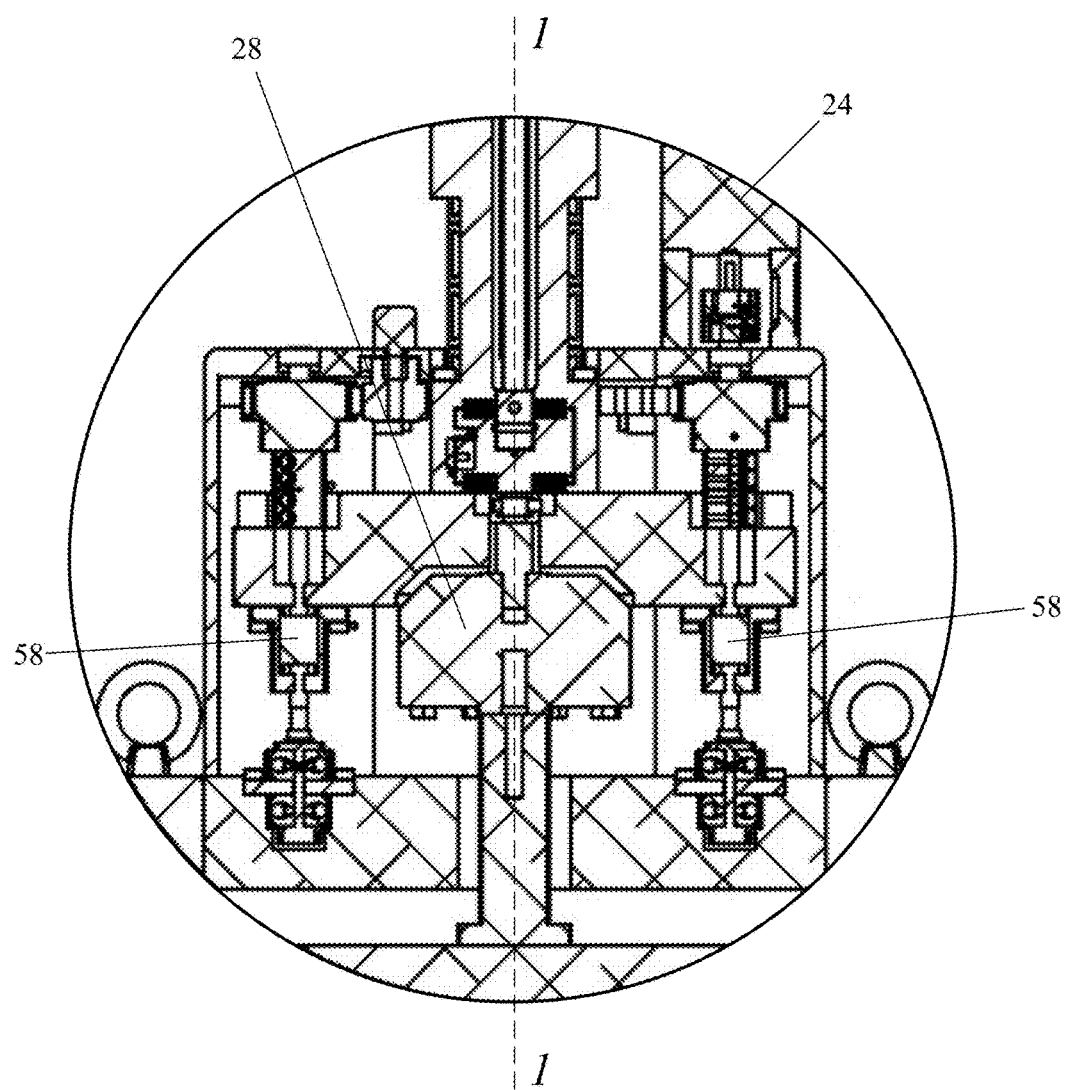
FIG. 4 shows a broken out sectional view within circle 4 of FIG. 1 showing the motor and screw drive assembly.

FIG. 4 shows the motor and screw drive in the upper part of the sample manipulator. In some embodiments, the motor and screw drive is used to apply a predetermined load to the sample 99. The top axial motion cross support drive motor 24 actuates one or both of the vertical screws 58 downward or upward to change the load on the sample. The sample load cell 28 measures the load on the sample and the vertical screws 58 may be adjusted until a desired predetermined load is being applied to the sample 99. In other embodiments, the piezoactuators 22, 26 aid, either alone or in conjunction with the motor and screw drive, in applying the predetermined load to the sample, by pushing or pulling on the sample or synchronously translating the sample along the rotational axis 1 while the load on the sample is varied by the motor and screw drive.

Figure 5:
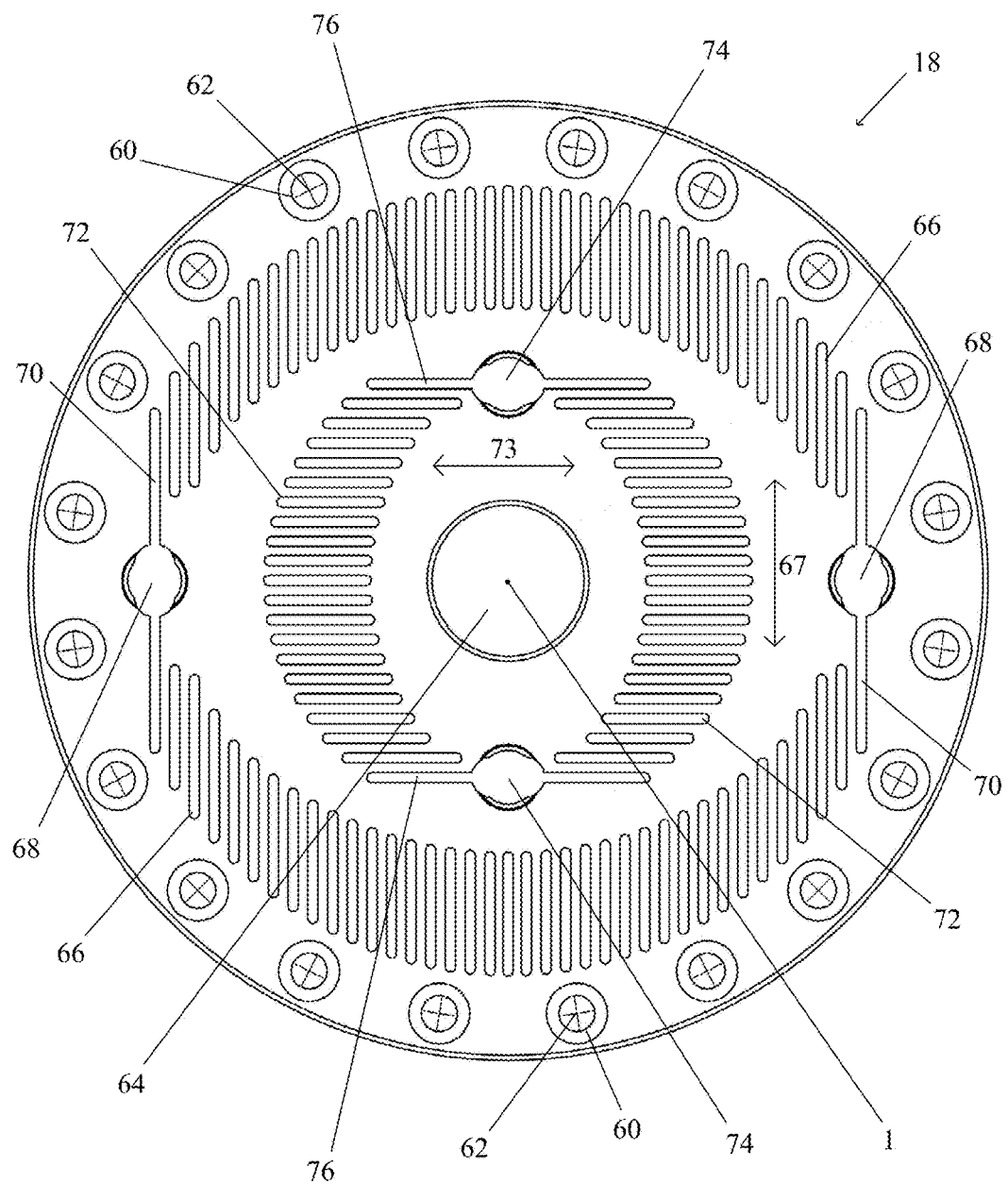
FIG. 5 shows a top view of the x-y flexure of the measuring instrument of FIG. 1.

Referring to FIG. 5, the sample alignment flexure plate 18 has an annular plate shape and includes a plurality of flexure mounting holes 60 evenly spaced around the periphery of the plate 18 with fasteners 62, which are preferably screws, in the flexure mounting holes 60 mounting the sample alignment flexure plate 18 to the bottom fluid bearing spool 16. Although twenty flexure mounting holes 60 are shown in FIG. 5, other numbers of holes may be used within the spirit of the present invention. The number of flexure mounting holes 60 is preferably a multiple of four and alternative preferred numbers of flexure mounting holes 60 include, but are not limited to, 12, 16, 24, 28, or 32. The sample alignment flexure plate 18 also includes a sample mounting hole 64 through the center of the plate 18, with the rotational axis 1 at the center of the sample mounting hole 64.

A plurality of oblong parallel flexure veins 66 in the x-direction (a first oblong direction 67 perpendicular to the rotational axis 1) are located radially between the flexure mounting holes 60 and the sample mounting hole 64. The flexure veins 66 preferably all have the same size and oblong shape. Although seventy flexure veins 66 in the x-direction are shown in FIG. 5, other numbers of veins may be used within the spirit of the present invention. The number of flexure veins 66 in the x-direction is preferably even and is preferably in the range of forty to one hundred and more preferably is in the range of sixty to eighty. Two tapered x-direction threaded holes 68 are located 180° from each other within long flexure veins 70 in the x-direction. A plurality of parallel flexure veins 72 in the y-direction (a second oblong direction 73 perpendicular to the rotational axis 1 and perpendicular to the first oblong direction 67) are located radially between the flexure mounting holes 60 and the flexure veins 66 in the x-direction. The flexure veins 72 preferably all have the same size and oblong shape. Although thirty-eight flexure veins 72 in the y-direction are shown in FIG. 5, other numbers of veins may be used within the spirit of the present invention. The number of flexure veins 72 in the y-direction is preferably even and is preferably in the range of twenty to fifty-six and more preferably is in the range of thirty to forty-six. Two tapered y-direction threaded holes 74 are located 180° from each other, 90° from the tapered x-direction threaded holes 68, and within long flexure veins 76 in the y-direction. Although the veins are described specifically as "x-direction" and "y-direction", the names of these two perpendicular directions is arbitrary, and "x-direction" and "y-direction" may alternatively be reversed in the previous description without affecting operation of the system. Four tapered screws in the tapered threaded holes 68, 74 move the sample position when they are tightened for fine adjustment by pushing the flexure and creating motion for sample alignment in one direction depending on which screw is adjusted, either by tightening or loosening. These adjustments may be done either manually by hand or automatically by the control system for the sample manipulator.

Figure 6:
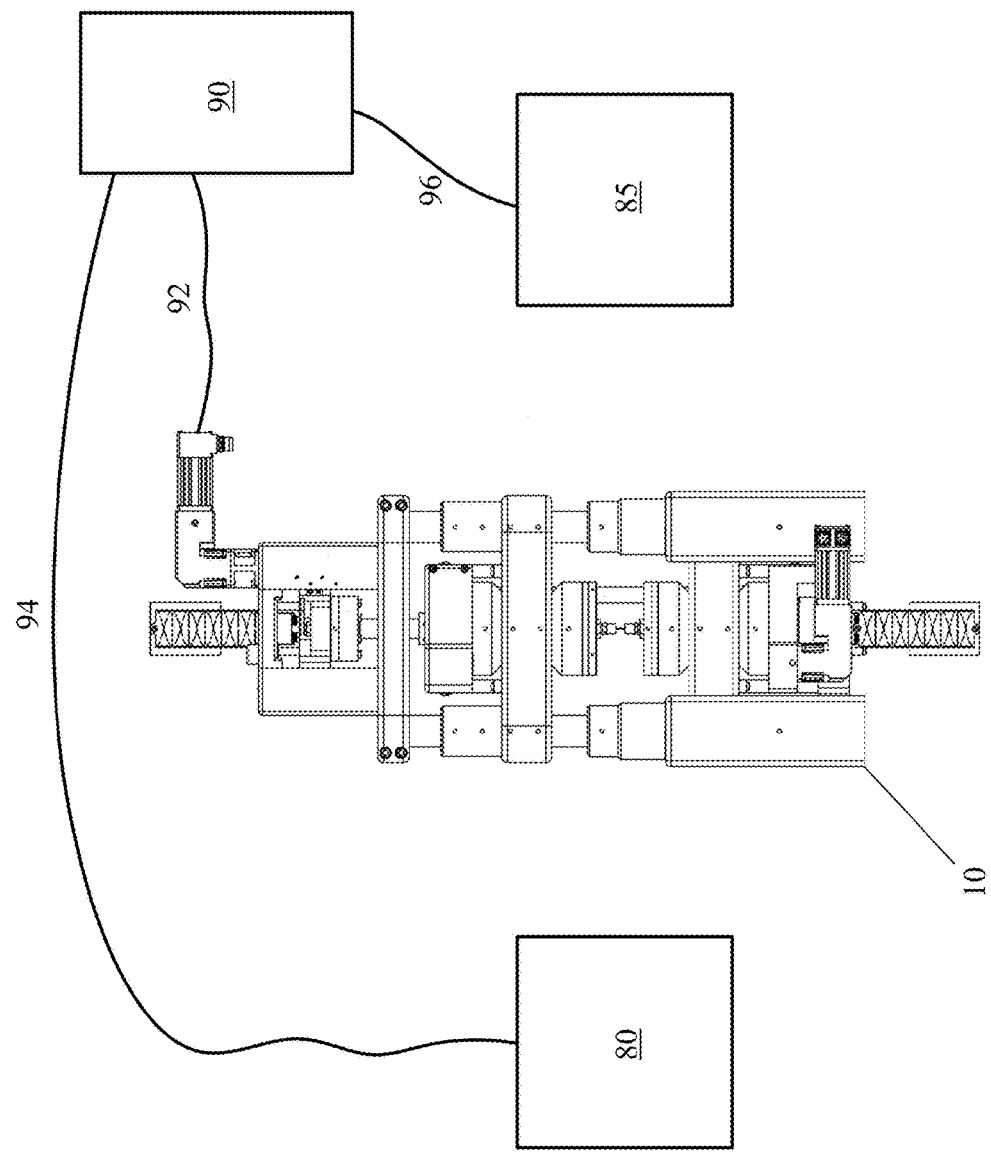
FIG. 6 shows schematically a high-precision tomography system in an embodiment of the present invention.

Referring to FIG. 6, a high-precision tomography system includes a sample manipulator 10, a penetrating wave source 80, a detector 85, and a processor 90. The processor 90 directs the sample manipulator 10, the penetrating wave source 80, and the detector 85 by way of communication lines 92, 94, 96, respectively. These communication lines 92, 94, 96 may be any conventional wired or wireless communication lines. Although the sample manipulator 10, the penetrating wave source 80, the detector 85, and the processor 90 are shown as separate physical units in separate housings in FIG. 6, any two or more may be located within a common housing within the spirit of the present invention.

Experimental testing was done with a sample manipulator similar to the design shown in FIG. 1 in an experimental system. Encoder pulse counts were collected with one degree motions, spanning 360 degrees at three different speeds: 0.1 degrees per second, 1 degree per second, and 10 degrees per second. The encoders were on two air bearings. The bottom bearing was driven directly by the servo motor, while the top was the "follower." Motion was controlled by the servo feedback, not directly by the rotation encoders, which was determined to be the more stable way to run the high-precision system.

The calibration was determined to be 1.373 arcseconds per encoder pulse (taking 2622 pulses per degree as the average), which was consistent with expectations (1.37 was the number expected). This corresponded to 0.381 millidegrees per pulse.

At all speeds, the one degree motions had a ≈12.5 pulse-count standard deviation or 0.0048 degree on the driven rotation and slightly larger on the follower. There was some regularity in the fluctuations, most clearly seen in the difference counts. A high frequency component had a period of about 7.1 degrees (about 50 periods per 360 degree rotation) and had a repeatable phase over different speeds. A slower oscillation had about a 60 degree period (6 per complete rotation) but was less well-defined. These may be a result of the structure of the drive belt. Overall, the high-precision system was found to run stably over the range of speeds tested with a consistency of motion without dramatic outliers on many trial runs over two orders of magnitude in speed.

Although the results in the above-described experimental testing were excellent, additional testing and improvements to the encoders and drive belts are expected to provide a sample manipulator with even greater precision than reported in the above-described experimental system.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A sample manipulator for high-precision manipulation of a sample, the sample manipulator comprising:
    a sample stage comprising a sample holder for receiving the sample and maintaining the sample on a rotational axis, the sample stage having a top and a bottom;
    a first fluid bearing spool coupled to the top of the sample stage;
    a first fluid flow rotation shaft rotatable within a first fluid flow rotation bushing and coupled to the first fluid bearing spool, the first fluid flow rotation shaft being rotatable about the rotational axis;
    a first actuator operatively coupled to actuate the first fluid bearing spool axially along the rotational axis;
    a second fluid bearing spool coupled to the bottom of the sample stage;
    a second fluid flow rotation shaft coaxial with the first fluid flow rotation shaft, rotatable within a second fluid flow rotation bushing, and coupled to the second fluid bearing spool, the second fluid flow rotation shaft being rotatable about the rotational axis; and
    a second actuator operatively coupled to actuate the second fluid bearing spool axially along the rotational axis;
    wherein the first fluid bearing spool and the second fluid bearing spool are fluid flow bearing assemblies containing a fluid;
    wherein the first flow rotation shaft and the second flow rotation shaft share the same rotational axis;
    wherein the first actuator and the second actuator, in combination, cause a load to be applied to the sample in the sample holder when the sample is manipulated through 360 degrees of high precision continuous sample rotation through:
        actuation of the first fluid bearing spool by the first actuator axially along the rotational axis of the first flow rotation shaft coupled to the top of the sample stage through the first fluid bearing spool and
        actuation of the second fluid bearing spool by the second actuator axially along the rotational axis of the second flow rotation shaft coupled to the bottom of the sample stage, and
    wherein the first fluid bearing spool and the second fluid bearing spool resist axial motion and radial motion when the sample is manipulated through the 360 degrees of high precision continuous sample rotation.

2. The sample manipulator of claim 1, wherein the fluid is selected from the group consisting of compressed air and oil.

3. The sample manipulator of claim 1 further comprising:
    a rotation motor;
    a first drive pulley driven by the rotation motor;
    a first idle pulley driven by the rotation motor;
    a first driven pulley, located between the first drive pulley and the first idle pulley, coaxial with and rotatable with the first fluid flow rotation shaft, and driven by a top drive belt driven by the first drive pulley and the first idle pulley, the first drive belt coupling the first driven pulley to the first drive pulley and the first idle pulley;
    a second drive pulley driven by the rotation motor;
    a second idle pulley driven by the rotation motor;
    a second driven pulley, located between the second drive pulley and the second idle pulley, coaxial with and rotatable with the second fluid flow rotation shaft, and driven by a second drive belt driven by the second drive pulley and the second idle pulley, the second drive belt coupling the second driven pulley to the second drive pulley and the second idle pulley.

4. The sample manipulator of claim 1 wherein the first actuator and the second actuator are piezoelectric actuators.

5. The sample manipulator of claim 4, wherein the first piezoelectric actuator and the second piezoelectric actuator, in combination, cause the load to be applied to the sample in the sample holder.

6. The sample manipulator of claim 5, wherein the load is of a type selected from the group consisting of a compressive load and a tensile load.

7. The sample manipulator of claim 1, wherein the sample stage further comprises a first flexure plate coupled to a top of the sample holder and to a bottom of the first fluid bearing spool, and a second flexure plate coupled to a bottom of the sample holder and to a top of the second fluid bearing spool.

8. The sample manipulator of claim 7, wherein each of the first flexure plate and the second flexure plate comprises a monolithic flexure body having:
    a central axis;
    a top surface;
    a bottom surface;
    a radial surface;
    a sample mounting hole extending through the top surface and the bottom surface and having a sample mounting hole center coaxial with the central axis;
    a plurality of flexure mounting holes extending through the top surface and the bottom surface and spaced around a periphery of the monolithic flexure body;
    a plurality of first veins extending through the top surface and the bottom surface and spaced radially around the sample mounting hole, each first vein having an oblong shape extending in a first oblong direction perpendicular to the central axis;
    a first pair of tapered threaded holes, each of the first pair of tapered threaded holes being formed through one of the plurality of first veins, the first pair of tapered threaded holes being located 180 degrees from each other in the monolithic flexure body;
    a plurality of second veins extending through the top surface and the bottom surface and spaced radially around the plurality of first veins, each second vein having an oblong shape extending in a second oblong direction perpendicular to the central axis and perpendicular to the first oblong direction;
a second pair of tapered threaded holes, each of the second pair of tapered threaded holes being formed through one of the plurality of second veins, the second pair of tapered threaded holes being located 180 degrees from each other and 90 degrees from each of the first pair of tapered threaded holes in the monolithic flexure body; and
at least one tapered threaded screw received within one of the first pair of tapered threaded holes and the second pair of tapered threaded holes;
wherein the tapered threaded holes, the tapered threaded screw, and the veins are formed such that when the tapered threaded screw is adjusted, a side of the tapered threaded screw applies a force to the monolithic flexure body, thereby bending the monolithic flexure body to provide fine, precise sub-micron control movement of a sample mounted in the sample mounting hole.

9. The sample manipulator of claim 1 further comprising:
a first vertical screw actuatable to apply a first portion of a load to the sample;
a second vertical screw actuatable to apply a second portion of the load to the sample; and
a drive motor coupled to selectively actuate the first vertical screw and the second vertical screw.

10. The sample manipulator of claim 9 further comprising a sample load cell located above the sample holder for measuring the load on the sample.

11. A method of manipulating a sample comprising the steps of:
a) placing the sample in a sample holder of a sample manipulator, the sample manipulator comprising:
a sample stage comprising the sample holder for receiving the sample and maintaining the sample on a rotational axis, the sample stage having a top and a bottom;
a first fluid bearing spool coupled to the top of the sample stage;
a first fluid flow rotation shaft rotatable within a first fluid flow rotation bushing and coupled to the first fluid bearing spool, the first fluid flow rotation shaft being rotatable about the rotational axis;
a first actuator operatively coupled to actuate the first fluid bearing spool axially along the rotational axis;
a second fluid bearing spool coupled to the bottom of the sample stage;
a second fluid flow rotation shaft coaxial with the first fluid flow rotation shaft, rotatable within a second fluid flow rotation bushing, and coupled to the second fluid bearing spool, the second fluid flow rotation shaft being rotatable about the rotational axis;
a second actuator operatively coupled to actuate the second fluid bearing spool axially along the rotational axis;
wherein the first fluid bearing spool and the second fluid bearing spool are fluid flow bearing assemblies containing a fluid;
wherein the first flow rotation shaft and the second flow rotation shaft share the same rotational axis;
b) actuating at least one of the first fluid bearing spool and the second fluid bearing spool via the first actuator and the second actuator in combination to cause a load to be applied to the sample holder and to move the sample holder and the sample axially to manipulate the sample through 360 degrees of high precision continuous sample rotation, wherein the first fluid bearing spool and the second fluid bearing spool resist axial motion and radial motion when the sample is manipulated through the 360 degrees of high precision continuous sample rotation and
c) collecting angular data of the sample through the 360 degrees of high precision continuous sample rotation.

12. The method of claim 11, wherein the first actuator and the second actuator are piezoelectric actuators.

13. The method of claim 11 further comprising the step of:
d) actuating a rotation motor to rotate the sample and the sample stage around the rotational axis, the sample manipulator further comprising:
the rotation motor;
a first drive pulley driven by the rotation motor;
a first idle pulley driven by the rotation motor;
a first driven pulley, located between the first drive pulley and the first idle pulley, coaxial with and rotatable with the first fluid flow rotation shaft, and driven by a first drive belt driven by the first drive pulley and the first idle pulley, the first drive belt coupling the first driven pulley to the first drive pulley and the first idle pulley;
a second drive pulley driven by the rotation motor;
a second idle pulley driven by the rotation motor;
a second driven pulley, located between the second drive pulley and the second idle pulley, coaxial with and rotatable with the second fluid flow rotation shaft, and driven by a second drive belt driven by the second drive pulley and the second idle pulley, the second drive belt coupling the second driven pulley to the second drive pulley and the second idle pulley.

14. The method of claim 11 further comprising the step of:
d) applying a predetermined load to the sample using a motor and screw drive comprising:
a first vertical screw actuatable to apply a first portion of the predetermined load to the sample;
a second vertical screw actuatable to apply a second portion of the predetermined load to the sample; and
a drive motor coupled to selectively actuate the first vertical screw and the second vertical screw.

* * * * *